United States Patent [19]

Isnardon et al.

[11] Patent Number: 4,893,490
[45] Date of Patent: Jan. 16, 1990

[54] DEVICE AND PROCESS FOR CONTROLLING THE EFFECTIVENESS OF PARTICLE HAMMERING OF THE INNER SURFACE OF A STEAM GENERATOR TUBE

[75] Inventors: Gerald Isnardon, Nanterre; Paul Jacquier, Tassin la Demi-Lune; Lylvie Voisembert, Heyrieux, all of France

[73] Assignee: Framatome, Courbevoie, France

[21] Appl. No.: 168,059

[22] Filed: Mar. 14, 1988

[30] Foreign Application Priority Data

Mar. 13, 1987 [FR] France ................................ 8703484

[51] Int. Cl.$^4$ .......................................... B23P 15/26
[52] U.S. Cl. ...................................... 72/53; 29/90.7; 51/411; 51/415; 51/320
[58] Field of Search ............... 72/53, 10; 51/411, 320, 51/410, 319, 415; 29/90.7, 727, 726

[56] References Cited

U.S. PATENT DOCUMENTS

| 3,906,780 | 9/1975 | Baldwin | 73/61 R |
| 4,499,769 | 2/1985 | Conway | 72/10 |
| 4,641,510 | 2/1987 | Mitsching et al. | 72/53 |
| 4,713,882 | 12/1987 | Bianchi et al. | 72/53 |

FOREIGN PATENT DOCUMENTS

| 0181810 | 5/1986 | European Pat. Off. |  |
| 0014290 | 2/1977 | Japan | 51/415 |
| 43836 | 6/1979 | Japan |  |
| 187853 | 11/1983 | Japan |  |
| 216050 | 12/1984 | Japan |  |
| 7411393 | 8/1974 | Netherlands |  |

Primary Examiner—David Jones
Attorney, Agent, or Firm—Pollock, Vande Sande & Priddy

[57] ABSTRACT

The hammering is carried out by a device having a tubular outer housing (5) which is placed against a face of the tube plate around a flush end of the tube to be hammered. A tool comprising a nozzle for projecting particles is mounted for axial movement in the outer housing (5). The control device has at least one piezoelectric sensor (20) in contact with the wall of the outer housing (5) and apparatus for measuring (23, 24) the electrical signal generated in the sensor (20). The nozzle for projecting particles is introduced into the outer housing (5) at the height of the sensors (20) after each tube hammering operation. The electrical voltage of the signals produced by the sensors is measured.

8 Claims, 2 Drawing Sheets

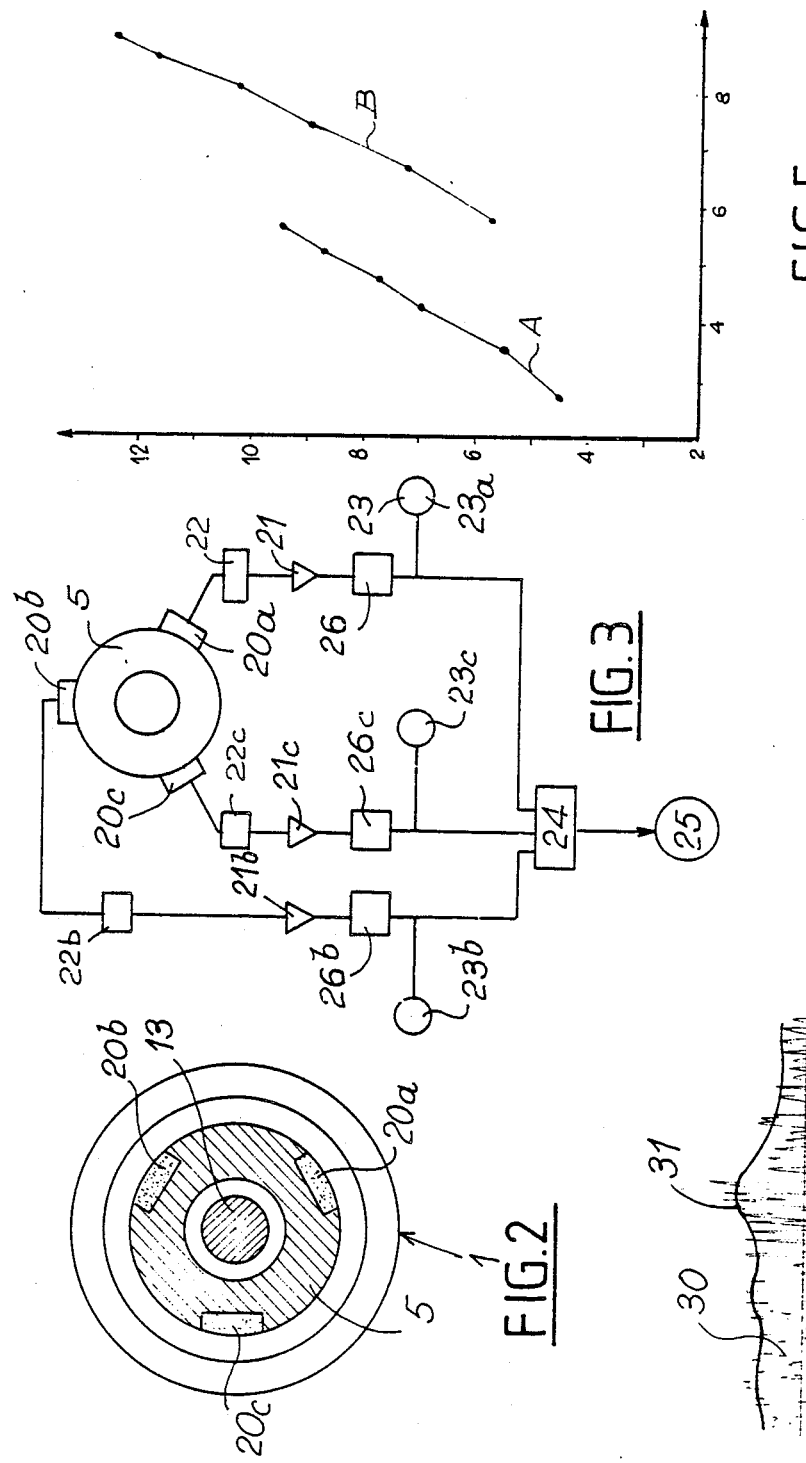

DEVICE AND PROCESS FOR CONTROLLING THE EFFECTIVENESS OF PARTICLE HAMMERING OF THE INNER SURFACE OF A STEAM GENERATOR TUBE

FIELD OF THE INVENTION

The invention relates to a device and process for controlling the effectiveness of particle hammering of the inner surface of a steam generator tube set into a tube plate.

BACKGROUND OF THE INVENTION

It is known to carry out hammering of the inner surface of a steam generator tube using particles suspended in a gas travelling at high speed, in order to produce a compression of the inner wall of the tube, especially in the regions of this tube which are liable to be affected by stress corrosion.

A process of this kind and a device for implementing are disclosed in applicants' French Pat. Nos. 2,572,965 and 2,584,320.

This process for producing compression may be applied in particular to the steam generator tubes of press-urized-water nuclear reactors, whose inner diameter is close to 0.020 m. The size of the particles employed for the hammering, the mass flow rate of these particles, and the speed of the carrier gas must be set at accurate values, in order to ensure high effectiveness of the operation of producing compression of the sensitive regions of the inner surface of the tube.

This operation is performed inside the water box of the steam generator, under remote control, by the use of a device comprising an outer housing of tubular shape comprising, at one of its ends, a bearing face which is intended to come into contact with the entry face of the tube plate, in succession around the end of each of the tubes to be treated, which are flush with this entry face. A hammering tool, comprising a nozzle for projecting particles suspended in the carrier gas, is fastened to the end of a flexible sheath and is mounted for movement in the axial direction, in relation to the outer housing. In order to perform the hammering of a tube, the outer housing is placed with its end face in contact with the entry face of the tube plate, around the tube to be treated. The hammering tool is introduced into the tube and is moved inside this tube as far as the region to be treated.

The treatment is then carried out by projection of the particles by means of the carrier gas, the projection nozzle being moved at a low speed in the region to be treated.

The hammering operation must be performed in succession on a very large number of tubes, since steam generators of pressurized-water nuclear reactors contain several thousand tubes. Moreover, these tubes are not accessible during the treatment for producing compression, or after such treatment, because of their radioactivity. The effectiveness of the treatment for producing compression cannot therefore be verified using simple means and a direct method.

One prior art method for measuring the effectiveness of a particle hammering treatment, such as microbead blasting or shot blasting, consists in using a specimen of a standardized type known by the name of Almen, on which the particle hammering operation is performed. French Standard NF L 06,832 of December 1979 accurately defines the test method and the parameters defining the effectiveness of hammering. In particular, the covering of this hammering is determined, and is defined as the ratio of the imprinted area to the area to be hammered or shot-blasted.

A known method for measuring the effectiveness of microbead blasting of the inner surface of a tube, i.e., the hammering of this area with fine beads, consists in carrying out the treatment on a tube of the same diameter and of the same thickness as the tubes to be treated. After the treatment has been performed on the test tube, a slit is made in the surface of this tube, along a generatrix, and then the tube diameter is measured after the slit has been cut. The relative change in the tube diameter is calculated, after the slit has been cut. This value is representative of the effectiveness of the hammering performed on its inner surface. This method has the disadvantage of being time-consuming and of requiring many handling operations in order to produce one measurement of the effectiveness of hammering.

In the case of the treatment of a steam generator of a pressurized-water nuclear reactor, the prior art control methods which are described above can be employed only at regular intervals, after the treatment of a certain number of tubes and outside the water box of the steam generator.

When the control is performed on Almen specimens, during the treatment of producing compression by hammering the tubes of a steam generator, a control is generally carried out on a specimen at regular intervals, after the hammering of a batch of several hundred tubes, for example three hundred tubes, has been performed. To do this, the tool must be withdrawn from the water box of the steam generator, and hence the tube treatment operation must be stopped.

Under the environmental conditions prevailing in the vicinity of the steam generator and, in particular, because of the existence of some radioactivity of the elements employed, certain precautions must be taken to protect the personnel working on the site.

Under these conditions, the time devoted to all the control operations represents approximately 10% of the total time devoted to the operation of producing compression by hammering.

Furthermore, if the control detects a shortcoming in the treatment, the whole batch of tubes whose hammering has been carried out since the last control must be retreated. It is not possible, in fact, to determine from which tube onwards the hammering treatment has turned out to be defective.

No device is known to date which would make it possible to control the effectiveness of an operation of hammering the inner surface of a steam generator tube and to provide information immediately after the hammering of the tube and without having to interrupt the hammering operation taking place.

SUMMARY OF THE INVENTION

The purpose of the invention is therefore to propose a device for controlling the effectiveness of particle hammering of the inner surface of a steam generator tube set into a tube plate, the hammering being performed by means of a device comprising a tubular outer housing whose end face is placed against a face of the tube plate around a flush end of the tube, and a tool mounted for axial movement in the outer housing, comprising a nozzle for projecting particles conveyed by a gas at high speed and fastened to the end of a flexible sheath, this device permitting immediate and in-line control of the effectiveness of the hammering, requiring no disassembly of the tool and no interruption of the hammering operation.

To this end, the control device according to the invention comprises at least one piezoelectric sensor arranged in contact with the wall of the outer housing, in the vicinity of its end bearing against the tube plate, and means for measuring the electrical signal generated in the sensor.

The invention also relates to a control process employing the device according to the invention and making it possible to avoid a stoppage of the hammering operation and losses of time.

BRIEF DESCRIPTION OF THE DRAWINGS

In order that the invention may be more clearly understood, a description will now be given, with reference to the appended drawings, of an embodiment of a device according to the invention and its use for controlling the effectiveness of an operation of internal hammering of the tubes of a steam generator of a pressurized-water nuclear reactor.

FIG. 2 is a view along line 2—2 of FIG. 1.

FIG. 3 is a general diagrammatic view of the whole of the control device according to the invention.

FIG. 4 is an illustration of the electrical signals provided by the sensors of the control device.

FIG. 5 is a calibration curve which gives the correlation between the measurements performed using the control device according to the invention and the corresponding measurements on Almen specimens.

DESCRIPTION OF PREFERRED EMBODIMENT

Figure 1:
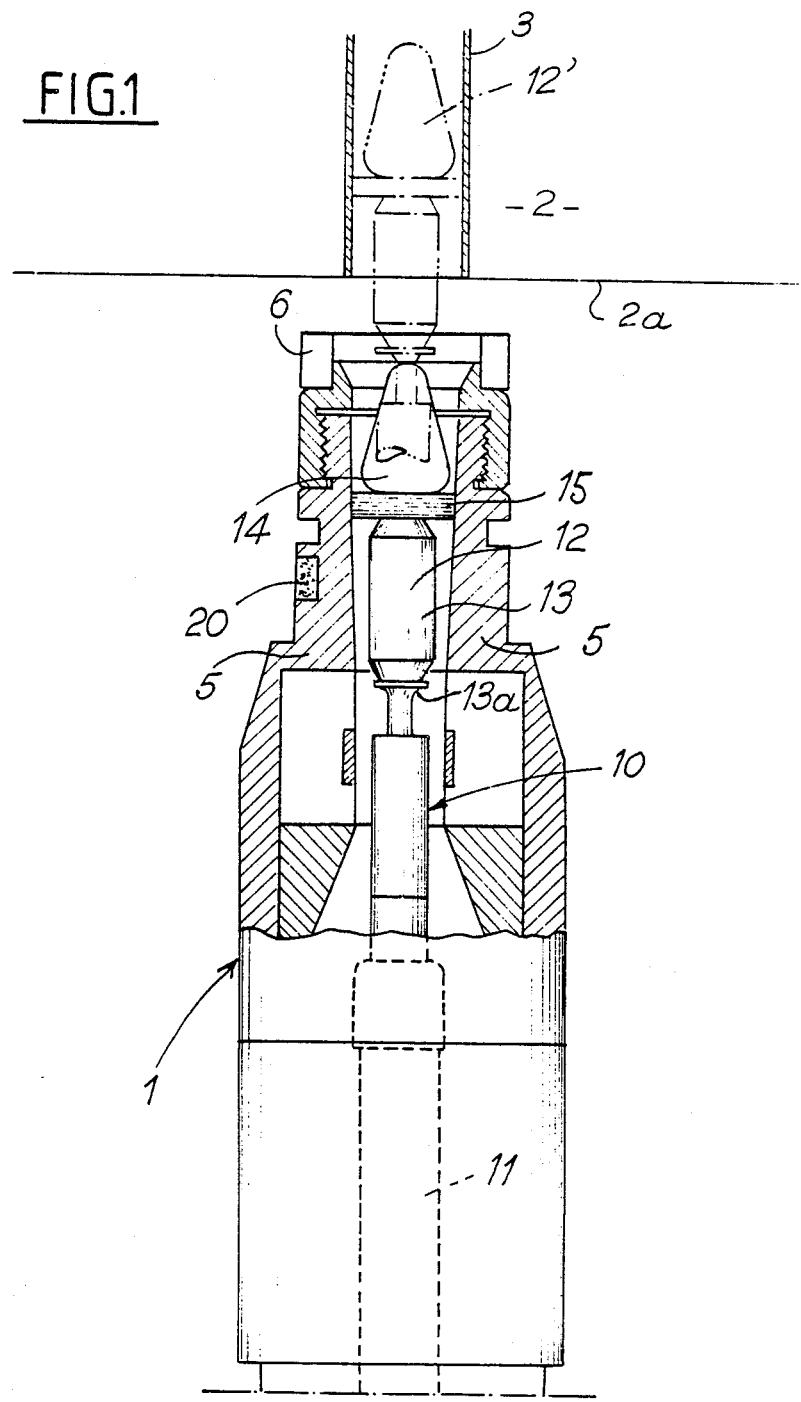
FIG. 1 is a view, in section through a vertical plane of symmetry, of a hammering device equipped with piezoelectric sensors of a control device according to the invention.

FIG. 1 shows the end of a hammering tool 1 in position inside the water box of a steam generator, vertically in line with a tube 3 of this steam generator, which is set into the tube plate 2.

The tool 1 comprises an outer housing 5 of tubular shape comprising an end 6 consisting of a bearing ring whose inner diameter is larger than the diameter of the tube 3.

In order to perform the hammering in the tube 3, the tool 1 is positioned under the entry face 2a of the tube plate 2, by means of a remotely-controlled handling device, so that the ring 6 comes to bear on this face 2a, around the end of the tube 3 which is flush with this face 2a.

The hammering tool 1 comprises a movable part 10 mounted axially inside the tubular outer housing 5 and consisting of a particle-projection nozzle 12 fastened at the end of a flexible tube 11. At the end of the tool remote from the end shown in FIG. 1, the flexible tube 11 is connected to means for injecting a gas carrying the particles in suspension.

The outer housing 5 is connected to a suction system enabling a depressurization to be established in the annular space included between the inner surface of the housing 5 and the flexible conduit 11.

The nozzle 12 comprises a body 13 forming a profiled section 13a and bearing an end part 14 of profiled shape enabling the movable section 10 of the tool to be inserted into the tube 3, by movement in the vertical direction and upwards (position 12' of the nozzle shown by broken lines). The nozzle 12 also comprises a guiding device 15 consisting of a brush formed by radially directed flexible fibres of a length which permits guidance with a slight friction inside the tube 3.

The profiled section 13a of the nozzle enables the particles suspended in the gas stream to be directed as they leave the conduit 11, in directions which are practically radial in relation to the inner part of the outer housing 5 and of the tube 3.

As can be seen in FIGS. 1 and 2, three piezoelectric sensors 20a, 20b and 20c are placed in the side wall of the outer housing 5, in the vicinity of the end section 6 of this housing, by which it bears on the entry face 2a of the tube plate when the hammering device is in operation.

The three piezoelectric sensors 20a, 20b and 20c are arranged at 120° from each other, on the periphery of the outer housing 5, as can be seen in FIG. 2. These piezoelectric sensors are inserted into the wall of the housing 5 so that very good contact is ensured between this wall and the sensors.

As can be seen in FIG. 3, the piezoelectric sensors are each connected to a system for processing the electrical signals which they are liable to provide in the case where they are subjected to an external mechanical stress. Each of the processing systems comprises a filter 22, an amplifier 21, an integrating module 26 and a measuring apparatus 23. The amplifier 21, the filter 22 and the integrating module 26 are arranged in series, and the output of the module 26 is connected to a signal summer 24 which is common to the three processing systems associated with the sensors 20a, 20b and 20c, respectively. The measuring apparatus 23, which is a voltage-measuring apparatus, is arranged as a branch at the output of the module 26.

The filters 22 are of the high pass type with a cutoff frequency of 100 kHz.

An electrical voltage measuring apparatus 25 is also arranged at the output of the electrical signal summer 24.

The piezoelectric sensors 20 have a wide pass band ranging from 100 kHz to 2 MHz.

The treatment for producing compression by hammering on the tube 3 is carried out by inserting the mobile unit 10 into the tube, a jet of particles in a gas at very high speed being caused to travel in the flexible conduit 11 and directed radially towards the wall of the tube by the profiled section or tulip head 13a. At the end of the treatment, the movable unit 10 is lowered back inside the outer housing 5 of the hammering tool, without interruption of the circulation of the gas carrying particles. When the tulip head 13a reaches the height of the piezoelectric sensors 20, the particles which hit the inner wall of the outer housing 5 produce ultrasonic waves which are transmitted to the sensors 20. These waves are converted into electrical signals by the sensors 20. The electrical signals are then transmitted by each of the sensors to the corresponding processing system.

Under the conditions of hammering treatment of a steam generator tube, at a particle mass flow rate of 300 to 700 g/min, with the particles having a particle size close to 100 micrometers, the frequency of the ultrasonic waves induced by the impact of the particles on the wall of the outer housing 5 is of the order of 1 MHz. The electrical signals emitted by the sensors are processed by filters 22 and then amplified by the variable-gain amplifiers 21 whose gain setting may vary between 20 and 40 dB. An electrical signal is thus produced, whose maximum voltage amplitude is of the order of 3.5 V.

The electrical signals at the output of the amplifiers 21 are converted by the integrating modules 26.

FIG. 4 shows a picture of the electrical signal 30 at the output of the amplifiers 21 and of the electrical signal 31 at the output of the integrating modules 26. The signal 31 at the output of the modules forms an envelope signal representing the rate of changes in the root mean square value of the electrical signal 30.

The signals 31 at the output of the modules 26 are summed in the signal summer 24 and the resultant signal is transmitted to the voltmeter 25, which may be of analog or digital type.

The voltage measurement made by the voltmeter 25 may be considered to represent the effectiveness of the particle hammering treatment. In fact, the stream of particles hitting the inner surface of the housing 5 at the height of the sensors 20 is identical to the stream of particles which have produced the hammering of the tube 3, insofar as its intensity, its uniformity and the impact energy of the particles are concerned.

These particle flow characteristics are directly reflected in the spectral characteristics of the ultrasonic waves transmitted to the housing 5 and to the sensors 20, these waves being themselves converted into electrical signals by the piezoelectric sensors.

Before the hammering device is brought into operation, a sampling is performed, which consists in making, in parallel, tests on an Almen specimen and measurements using the device according to the invention, for various hammering intensities.

FIG. 5 shows the calibration curves obtained for a tube 19.2 mm in diameter (curve A) and one for a tube 22.4 mm in diameter (curve B). Along the ordinate axis, these curves give the effectiveness of the hammering treatment in Almen points, as a function of the voltage measured by the device according to the invention, which is plotted along the abscissa axis.

Curves A and B were obtained with a speed of travel of the nozzle 12 in the outer housing 5, at the height of the sensors 20, of 8.8 mm per second. The tests were carried out in the device according to the invention at a pressure varying between 1 and 3 bars.

A calibration operation must be performed at the outset of any hammering operation on the tubes of a steam generator, because the calibration curve may vary as a function of characteristics due to the plant.

The calibration curve established before each hammering operation makes it possible to adjust the various parameters of the treatment, such as the injection pressure of the particles and the depressurization of the return circuit for these particles. These values can vary as a function of the configuration and the length of the particles' path between the storage hoppers for these particles and the injection nozzle. A fine tuning of the pressure or calibration is thus carried before each hammering operation.

During the treatment, after each tube-hammering operation, the tool is lowered in the outer housing down to the level of the piezoelectric sensors and the total electrical voltage of the signals originating from the sensors is measured. This value may be converted into Almen points by using the calibration curve or may be employed directly to determine whether the effectiveness of the tube hammering is considered to be sufficient.

If the effectiveness is considered to be sufficient, the treatment is continued by moving the tool towards another tube and inserting the nozzle into this tube.

If the effectiveness of the treatment is considered to be insufficient, the hammering of the tube is carried out anew, after the setting of the operating parameters of the plant has been checked.

If the parameters reflect a treatment which remains defective, an intervention is necessary in the plant in order to determine the source of the deficiency and to remedy it.

In all cases, the effectiveness of the treatment is controlled immediately after the tube hammering and a deficiency of this treatment can be remedied immediately.

Furthermore, comparison of the measurements provided by the three voltmeters 23a, 23b and 23c makes it possible to check whether the hammering is performed by the nozzle in a uniform manner over the entire periphery of the housing or of the tube. In fact, in the case where the particle flow is perfectly uniform over the entire periphery of the housing or of the tube, the signals supplied by the sensors 20a, 20b and 20c are identical. In the event that a significant difference is detected between the measurements supplied by the three voltmeters 23a, 23b and 23c, a check is made on the tool in order to remedy this lack of uniformity in the distribution of the stream of particles.

This checking is also immediate, so that it is possible to ensure a treatment of each of the tubes which is completely controlled.

Any device for measuring, recording or displaying an electrical parameter representing the stresses received by the piezoelectric sensors 20 may be employed instead of voltmeters of an analog or digital type, in order to produce values representing the effectiveness of the hammering treatment.

In the case where a continuous recording of the voltages of the electrical signals supplied by the processing systems of the sensors is made, the entire history of the treatment of a steam generator can be reconstituted.

We claim:

1. Device for hammering the inner surface of a steam generator tube set into a tube plate, comprising a tubular outer housing having an end face for bearing on a face of the tube plate around a flush end of the tube, and a tool comprising a nozzle for projecting particles conveyed by a gas at high speed, said particles being conveyed to the nozzle by a flexible conduit which is fastened to said nozzle, said nozzle and flexible conduit being mounted for axial movement in the outer housing, wherein said device further comprises means for controlling the effectiveness of particle hammering of the inner surface of the steam generator tube, said means comprising at least one piezoelectric sensor arranged on a wall of the outer housing in the vicinity of said end face of said housing, and means for measuring an electrical signal generated in the sensor connected to the sensor by electrical connections.

2. Device according to claim 1, comprising at least two of said piezoelectric sensors (20a, 20b, 20c) distributed along the periphery of the outer housing (5).

3. Control device according to claim 2, comprising three of said piezoelectric sensors (20a, 20b, 20c) arranged at 120° from each other at the periphery of the outer housing (5).

4. Device according to claim 2, wherein each of the sensors (20a, 20b, 20c) is connected to a system for processing electrical signals (22, 26), the processing systems being themselves connected to a signal summer (24) at the output of which an apparatus for measuring electrical voltage (25) is arranged.

5. Device according to claim 4, wherein each of the systems for processing the electrical signals associated with a piezoelectric sensor comprises a filter (22), an amplifier (21) and an integrating module (26).

6. Device according to claim 4, wherein an apparatus for measuring electrical voltage (233) is arranged as a branch at the output of each of the processing systems (22, 26) before the summer (24).

7. Process for controlling the effectiveness of particle hammering of the inner surface of a steam generator tube (3) set into a tube plate (2), the hammering being performed by means of a device comprising a tubular outer housing (5) having an end face (6) bearing on a face (2a) of the tube plate (2), around a flush end of the tube (3), and a tool comprising a nozzle (12) for projecting particles conveyed by a gas at high speed and fastened at the end of a flexible conduit which supplies said particles, said nozzle and conduit being (11) mounted for axial movement in the outer housing (5), said process comprising the steps of (a) moving the nozzle (12) for projecting the particles into a position inside the outer housing (5), after having performed the hammering in a tube (3);

(b) projecting at high speed a jet of particles suspended in the gas which is identical to the jet of particles which has performed the hammering of the tube (3) onto the inner surface of the outer housing (5);

(c) converting the ultrasonic waves due to the impact of the particles against the outer housing (5) into electrical signals;

(d) measuring the amplitude of the electrical signals produced by the impact of the particles; and (e) using the measurement of the amplitude of the electrical signals to control the effectiveness of the hammering in the tube (3).

8. Control process according to claim 7, comprising the steps of (a) sensing and converting into electrical signals the ultrasonic waves produced by the particles in various positions around the housing (5);

(b) comparing the amplitudes of the various electrical signals obtained; and (c) determining whether a significant difference exists between the amplitudes of the various signals.

* * * * *

UNITED STATES PATENT AND TRADEMARK OFFICE
CERTIFICATE OF CORRECTION

PATENT NO.  : 4,893,490
DATED       : JANUARY 16, 1990
INVENTOR(S) : Gerard ISNARDON; Paul JACQUIER; Sylvie VOISEMBERT It is certified that error appears in the above-identified patent and that said Letters Patent is hereby corrected as shown below:

Title page, third inventor's first name should read:
--Sylvie--.

Signed and Sealed this

Fifteenth Day of October, 1991

Attest:

HARRY F. MANBECK, JR.

Attesting Officer

Commissioner of Patents and Trademarks